United States Patent [19]

Machovich et al.

[11] Patent Number: 4,530,964
[45] Date of Patent: Jul. 23, 1985

[54] PHARMACEUTICALLY ACTIVE COPOLYMERS, PROCESS FOR THEIR PREPARATION AND PHARMACEUTICAL COMPOSITIONS CONTAINING THEM

[75] Inventors: Raymund Machovich; Miklós Nagy; Judit Györgyi née Edelényi; István Horváth; Miklós Lów; Katalin Csomor; Egon Kárpáti; László Szporny; Lajos Kisfaludy, all of Budapest, Hungary

[73] Assignee: Richter Gedeon Vegyeszeti Gyar R.T., Budapest, Hungary

[21] Appl. No.: 478,468

[22] Filed: Mar. 24, 1983

[30] Foreign Application Priority Data

Mar. 31, 1982 [HU] Hungary .................. 974/82

[51] Int. Cl.$^3$ .................................. C08F 228/02
[52] U.S. Cl. .................................. 525/61; 525/60; 526/287
[58] Field of Search ............ 525/330.4, 330.6, 60, 525/61; 526/287

[56] References Cited

U.S. PATENT DOCUMENTS 2,989,514  6/1961  Jones .................................. 526/287
4,177,345 12/1979  Schweiger ........................ 525/61

Primary Examiner—Christopher A. Henderson
Attorney, Agent, or Firm—Karl F. Ross; Herbert Dubno

[57] ABSTRACT

The invention relates to new, pharmaceutically active copolymers with heparin-like activity, pharmaceutically acceptable salts thereof and a process for their preparation. The new copolymers comprise the units of the formula I

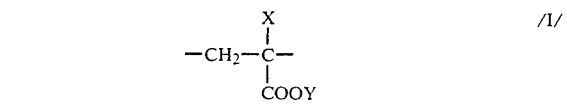

wherein X stands for hydrogen or methyl and Y is hydrogen, units of the formula III

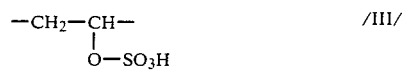

optionally units of the formula II

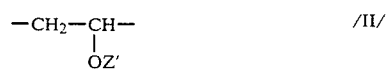

wherein Z' is hydrogen, and chain terminating units, formed from the units of the formulae I, III and optionally II under the conditions of copolymerization, in a statistical arrangement, and the pharmaceutically acceptable salts thereof, which contain, in addition to the above chain-members, units of the formulae IV and/or V

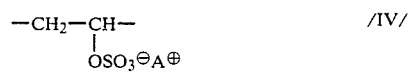

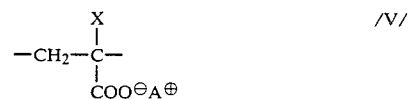

wherein A is a cation/ satisfactorily replace the organogenic heparin, or give a synergistic combination with that, 5 Claims, No Drawings

PHARMACEUTICALLY ACTIVE COPOLYMERS, PROCESS FOR THEIR PREPARATION AND PHARMACEUTICAL COMPOSITIONS CONTAINING THEM

FIELD OF THE INVENTION

The invention relates to new, pharmaceutically active copolymers, pharmaceutically acceptable salts thereof and a process for their preparation. The invention further concerns pharmaceutical compositions containing said copolymers or pharmaceutically acceptable salts thereof alone or in combination with further pharmaceutically active substances, e.g. heparin or a salt thereof, as active ingredient. Tissue-compatible prosthesis and coating materials are also within the scope of the invention.

BACKGROUND OF THE INVENTION

The anticoagulant activity of heparin was first reported by Howell et al. [Am. J. Physiol., 47, 328 (1918-19)]. The investigations carried out by Chargaff et al. [J. Biol. Chem. 115, 155 (1936)] on other natural and synthetic macromolecules with heparin-like activity revealed that the anticoagulant macromolecules always contain sulfate groups (e.g. heparin or potassium salt of the acidic sulfuric acid ester of polyvinylalcohol, prepared by said authors) but not all polymers containing sulfate groups show anticoagulant activity.

According to later publications, in contrast to the findings of Chargaff et al., there are described polymers which are potent anticoagulants, though they fail to contain sulfate groups [e.g. R. Machovich and I. Horváth: Thrombos. Res. 11, 765 (1977) and U.S. Pat. No. 3,844,989].

Until now the role of the sulfate groups has not unambiguously been made clear, and there is no polymer on the market which can satisfactorily replace the organogenic heparin having a varying composition.

OBJECT OF THE INVENTION

Our object was to prepare polymers containing sulfate groups, which are suitable for replacing heparin or can successfully be applied in combination with heparin.

DESCRIPTION OF THE INVENTION

It has been found that the new copolymers comprising units of the formula I

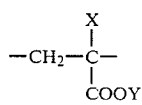

derived from (meth)acrylic acid or an ester thereof (X stands for hydrogen or methyl and Y is hydrogen), units of the formula III

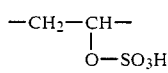

optionally units of the formula II

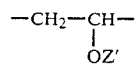

(Z' is hydrogen), and chain terminating units, formed from the units of formulae I, III and optionally II under the conditions of copolymerization, in a statistical arrangement, and the pharmaceutically acceptable salts thereof, which contain, in addition to the above chain members, units of the formulae IV and/or V

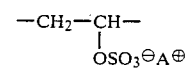

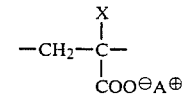

(X has the meaning defined above and A is a cation, preferably an alkaline metal or alkali earth metal ion) possess the desired properties.

The invention also comprises a process for preparing such solid copolymers comprising the steps of (a) copolymerizing a monomer of the formula Ia

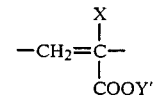

wherein X and Y' are hydrogen or methyl, with a vinyl alcohol monomer protected on the hydroxyl, having the formula IIa

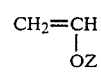

wherein Z is the acyl group of a lower alkanecarboxylic acid, preferably formyl, acetyl, haloacetyl, trifluoroacetyl, propionyl, or butyryl, as an ester protecting group, or a lower alkyl or aralkyl, preferably tert-butyl or benzyl, as an ether protecting group, and (b) eliminating the protecting groups (Z and the methyl group in place of Y') from the copolymer obtained in step (a), and (c) converting the deprotected copolymer obtained in step (b) into an acidic sulfuric acid ester or a pharmaceutically acceptable salt thereof.

The new copolymers according to the invention, similar to heparin, improve the antithrombin effect, i.e. increase the inactivation of thrombin which is responsible for blood clotting. They inhibit other protease enzymes contributing to the blood coagulation cascade and accordingly, the formation of thrombin. The copolymers according to the invention are therefore capable of preventing thrombosis due to increased coagulability of blood.

We have further found that the copolymers—unlike heparin—influence the blood clotting procedure also at another point of attack, since they inhibit the thrombin-fibrinogen reaction also directly (without antithrombin). The threshold concentration by which this anticoagulant mechanism is initiated amounts to 20 µg. of copolymer/ml. of plasma, in vitro.

According to animal tests, the copolymers of the invention have a more protracted anticoagulant effect than heparin. Alert rats were administered a single intravenous dose of a copolymer according to the invention and heparin, respectively, 30 minutes later a sample of blood was taken (with ether anaesthesia and subsequent heart puncture) and the anticoagulant activity was determined in the samples. While the blood clotting inhibitory effect of heparin decreased to one third of its original value in the 60th minute after treatment, the inhibitory effect of the copolymer according to the invention was half of the original level even 90 minutes after administration. In rabbits the maximum effect was observed 15 minutes after administration.

Heparin and the copolymer, when administered together, show a considerably higher activity than in the same dose administered separately, i.e. the combination has a synergistic effect.

It has further been found that by varying the proportion of free carboxylic groups to the acidic sulfate ester groups in the copolymer, the anticoagulant activity and, to a certain extent, the point of attack of the substance can be changed.

The anticoagulant activity of the copolymers according to the invention can be terminated by protamine sulfate, as is to that of heparin.

As a blood clotting inhibiting substance the copolymer is generally administered intravenously (injection, infusion) or subcutaneously.

To eliminate or reduce pains of the rheumatic type the copolymer is generally applied by local inunction (ointment, tincture).

The copolymer can further be employed as a coating material wherever clotting of blood is to be avoided. For example containers for storing blood samples and protheses for implantation (vessel walls, vessel catheters, etc.) can be coated by the copolymers according to the invention or can be prepared therefrom.

The copolymer is generally prepared with a polymerization degree of 50–3000, preferably 50–250 for anticoagulant purposes or against rheumatic pains. For application as a coating material or tissue-compatible prosthesis substance polymerization degrees of 50–3000, preferably exceeding 1000 are generally employed. Prostheses can be prepared also of a copolymer which has a polymerization degree below 1000 on a suitable carrier.

Preferably the new copolymers and pharmaceutically acceptable salts thereof are prepared by copolymerizing a monomer of the formula Ia, wherein X and Y' have the meanings given above, with a vinyl alcohol monomer, protected on the hydroxyl, having the formula IIa, in which Z has the same meaning as above, eliminating the protecting groups from the copolymer obtained, which contains 2 to 25 molar % of chain members derived from the monomers of the formula Ia, and converting the copolymer obtained, which is built up from chain members of the formulae I and II, in which Y and Z' stand for hydrogen, into a corresponding acidic sulfuric acid ester, in 2 to 100% related to the chain members of the formula II, and if desired converting the product obtained comprising units of the formulae I, III and optionally II [units of the formula III are preferably present in an amount of 5 to 40 molar %], and chain terminating units into pharmaceutically acceptable salts thereof, in which units of the formulae IV and V, wherein X and A are as defined above, are also present.

The invention further relates to pharmaceutical compositions comprising a copolymer containing units of the formulae I, III and optionally II and suitable chain terminating units with a polymerization degree of 50 to 3000, preferably 50 to 250 or pharmaceutically acceptable salts thereof and optionally further pharmaceutically active ingredients, in combination with conventional carriers and/or additives.

According to another aspect of the invention there is provided a coating substance or a prosthesis substance made of a copolymer comprising structural units of the formulae I, III and optionally II and corresponding chain terminating units, which has a polymerization grade of 50 to 3000, or salts thereof, and optionally carriers and/or auxiliary substances.

In the process according to the invention the copolymer is prepared from monomers of the formulae Ia and IIa. As a monomer of the formula Ia acrylic acid or methacrylic acid or esters thereof, are employed. The preferred representatives are acrylic acid methyl ester and methyl methacrylate. As a monomer of the formula IIa preferably vinyl acetate or a derivative thereof, e.g. vinyl chloroacetate, vinyl bromoacetate or vinyl trifluoroacetate; or other vinyl esters, e.g. vinyl formiate, vinyl propionate or vinyl butyrate are used. Certain vinyl ethers, in particular benzyl vinyl ether or tert-butyl vinyl ether can also be employed as starting substances.

Copolymerization is initiated in a conventional manner. Preferably free-radical initiators are employed, such as peroxides, hydrogen peroxides, azo compounds, particularly dibenzoyl-peroxide, acetyl peroxide, lauryl peroxide, t-butyl peroxide, 2,2'-azo-bis-isobutyronitrile.

In order to control the polymerization degree copolymerization is preferably performed in solution. The solvent used should be capable of dissolving both the monomer and the copolymer and initiators. First of all ester, e.g. methyl acetate, ethyl acetate, butyl acetate; alcohols, e.g. methanol; ketones, e.g. methyl ethyl ketone, acetone; and cyclic ethers, e.g. dioxane can be used as a solvent.

The monomers of the formula IIa are employed in an excess for the polymerization to avoid the formation of polyacrylic acid(ester).

The initiator is preferably employed in an amount of 0.1 to 0.5 g. per 100 g. of monomer and the monomer/solvent ratio is preferably kept in the range of 1:0.5–1:2.

Under the given conditions, between room temperature and the boiling point of the solvent, preferably at 40° to 90° C. the copolymerization takes about 2 hours, and the efficiency is good. When the desired degree of polymerization is achieved, the reaction is terminated for example by pouring on to ice water, and the coagulated product is isolated. If desired, the product can be purified by dissolution and subsequent recoagulation.

From the product of the first step of the process according to the invention the protecting groups are then eliminated.

The ester protecting groups can be eliminated by hydrolysis, alcoholysis or ammonolysis, preferably by hydrolysis, preferably under alkaline conditions. A total hydrolysis is preferred but the presence of about 0.1 to 2.0 molar % of remaining ester protecting groups is still acceptable.

The ether protecting groups can be eliminated by acidolysis or hydrolysis. Acidolysis is preferably carried out with hydrochloric acid or bromohydrogen, in the presence of water and/or an organic solvent.

After elimination of the protecting groups a solution, preferably an aqueous solution of the product is subjected to the following reaction step. If desired, however, the intermediate can also be isolated by evaporation and/or drying under mild conditions (film forming, lyophilization).

The product of he second reaction step is converted into an acidic sulfuric acid ester or a salt thereof. The esterification can be complete [all units of the formula II are esterified] or partial, depending on the amount of the esterifying agent.

As an esterifying agent preferably sulfuric acid is employed in an aqueous medium in an organic solvent, such as dimethyl formamide or in a mixture thereof with another solvent. The sulfuric acid can also serve as a medium for esterification, when employed in a sufficient amount. After esterification the product can be isolated by evaporation to dryness or lyophilization, after elimination of the excess reactant by dialysis. According to a preferred alternative, the esterified product is converted into a corresponding salt in situ by an alkaline material, e.g. sodium hydroxide, sodium carbonate, a suitable calcium compound, etc., and the product is isolated as a salt.

As an esterifying agent chlorosulfonic acid can also be employed in the presence of an organic solvent and a tertiary amine, preferably in pyridine or a mixture of pyridine and another organic solvent. In this case, if the reaction mixture containing the esterified product is treated with an alkaline reactant, the obtained salt contains in the place of $A^{\oplus}$ partly a pyridinium cation, partly a cation derived from the basis used. Therefore the reaction mixture is first diluted with water, dialyzed with an acid and subsequently with water in counterstream, and the preparation of salt is performed only after these steps. If chlorosulfonic acid is used, the esterification can be made practically complete.

The anticoagulant compositions containing the new copolymer as active ingredient are preferably formulated as injection or infusion solutions. The injection solutions contain distilled water or physiological saline solution as a carrier, optionally in admixture with preservatives, e.g. benzyl alcohol, antioxidants and buffers, etc.

The compositions optionally contain also further pharmaceutically active ingredients, e.g. adjuvants and heparin. Heparin and the copolymer according to the invention show a synergistic blood clotting inhibiting effect when used in a weight ratio between 0.1:1 and 1:0.1, preferably 1:1.

SPECIFIC EXAMPLES

The invention will now be illustrated in greater detail in the following specific Examples, which are given for illustration and not limitation of our invention.

EXAMPLE 1

(a) Copolymerization of acrylic acid and vinyl acetate

In a mixture of 60.4 ml (0.65 moles) of vacuum distilled vinyl acetate monomer and 64 ml. of dioxane 0.15 g. of benzoyl peroxide are dissolved, the reaction mixture is heated up to 75° C. and 2.5 ml. (0.037 mole) of vacuum distilled acrylic acid monomer are added dropwise. The reaction mixture is kept at 75° C. for 2 hours, whereupon it is poured into ice water under continuous stirring. The coagulated copolymer is isolated, or if desired, is dissolved in dioxane, coagulated in ice water, and the coagulate obtained is dried in a vacuum desiccator at 60° C. Yield: 47 g. (80%).

(b) Elimination of the protecting groups 40 g. of the copolymer prepared in the step (a) above are dissolved in 1000 ml. of 98% ethanol, the solution is heated up to 70° to 80° C., and a solution of 18 g. of sodium hydroxide in 450 ml. of distilled water is added in small portions. When the hydrolysis has taken place, the reaction mixture is neutralized with hydrochloric acid diluted with water in a ratio of 1:6, and is dialyzed chloride-free with distilled water, in counter-flow. The solution is concentrated, the dry substance content is determined and the copolymer content is adjusted to 10% by vol. by distilled water.

(c) Preparation of acidic sulfuric acid ester and salt thereof 150 ml. of an aqueous solution containing 10% by vol. of copolymer are poured into a round-bottom flask cooled with salt water and 350 ml. of concentrated sulfuric acid are added at a temperature of 5° to 10° C., portionwise in 2 hours, under continuous stirring. The reaction mixture is then kept at 5° C. for 24 hours, whereupon it is poured into a 4-times volume of distilled water cooled to 0° C. The solution is neutralized with anhydrous sodium carbonate and is desalted by dialysis in counter-flow with tap water and subsequently distilled water. The solution containing the sodium salt of the copolymer is concentrated, and if desired, a film is cast therefrom on a polyethylene foil. The film is dried in air and then in a vacuum desiccator at 40° C. Yield: 2 g. (70%) of copolymer, containing 8.5 molar % of acrylic acid-containing units or the sodium salt thereof, 30 molar % of units of polyvinyl alcohol origin converted into acidic sulfuric acid units or sodium salt thereof, and vinyl alcohol units up to 100%. The polymerization degree of the product is 60.

EXAMPLE 2

The procedure described in steps (a) and (b) of Example 1 is followed, except that the solution obtained after dialysis of the hydrolysate is partially concentrated, a film is cast therefrom on the top of a polyethylene foil, which is then dried, powered and 1 g. thereof is used to prepare the acidic sulfuric acid ester and its salt, respectively.

A mixture of 10 ml. of dimethyl formamide and 10 ml. of pyridine is cooled to 0° C., and 0.44 ml. of chlorosulfonic acid are added, followed by the addition of 1 g. of finely powdered copolymer. The reaction mixture is stirred at room temperature for one hour and at 60° C. for 2 subsequent hours. The reaction mixture is poured onto 60 g. of ice, and the solution is dialysed with 1 N sulfuric acid and subsequently with distilled water in counter-flow. The pH of the solution is adjusted to 8 with a 4 N aqueous sodium hydroxide solution, and the solution is evaporated to 15 ml. under reduced pressure, and the residue is lyophilized.

Yield: 2.4 g. (80%) of copolymer, which contains the total amount of the groups capable of conversion into sulfate ester groups as sulfate ester or a salt thereof.

EXAMPLE 3

Following the procedure described in steps (a) and (b) of Example 1 a copolymer containing 5 molar % of acrylic acid-containing units is prepared. The copolymer is converted to an acidic sulfuric acid ester according to step (c) of Example 1 with an amount of sulfuric acid, which corresponds to 48% by weight of the reaction mixture.

Yield: 95% of copolymer, containing 5 molar % of acrylic acid-containing units or sodium salt thereof, 4.5 molar % of vinyl alcohol sulfate units or sodium salt thereof and vinyl alcohol units up to 100%.

EXAMPLE 4

The procedure described in Example 3 is followed, except that the sulfuric acid is used in an amount corresponding to 60% by weight of the reaction mixture, and the reaction time is 48 hours.

Yield: 80% of copolymer, containing 13 to 15 molar % of vinylalcohol sulfate ester units or the sodium salt thereof.

EXAMPLE 5

The procedure described in Example 1 is followed, except that the copolymer prepared contains 5 molar % of methacrylic acid monomers instead of acrylic acid monomers, and sulfuric acid is used in an amount corresponding to 72% by weight of the reaction mixture.

Yield: 85% of copolymer, containing 5 molar % of methacrylic acid-containing units or the sodium salt thereof, 27 molar % of vinyl alcohol sulfate ester units or the sodium salt thereof, and vinyl alcohol units up to 100%.

We claim:

1. A copolymer having a polymerization degree of 50 to 3000 comprising units of the formula I

wherein
X is hydrogen or methyl,
Y is hydrogen, units of the formula III

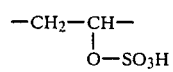

units of the formula II

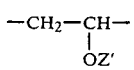

wherein Z' is hydrogen, and chain terminating units, formed from the units of formulae I, III and II under the conditions of copolymerization, in a statistical arrangement, or a pharmaceutically acceptable salt thereof, wherein the salts contain, in addition to the above units, units of the formula IV and/or V

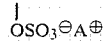

wherein A is a cation.

2. The copolymer defined in claim 1 which comprises units of polyvinyl alcohol of the Formula (II), units of polyacrylic acid or polymethacrylic acid of the Formula (I), and units of an acidic sulfuric acid polyvinylalcohol of the Formula (III).

3. A copolymer having a polymerization degree of 50 to 3000 comprising
units of the formula (I)

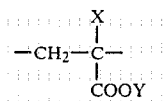

wherein
X is hydrogen or methyl; and
Y is hydrogen;
units of the formula (III)

and chain terminating units, formed from the units of formulae I and III under the conditions of copolymerization, in a statistical arrangement, or a pharmaceutically acceptable salt thereof, wherein the salt contains, in addition to the above units, units of formulae IV and/or V

wherein A is a cation.

4. The copolymer defined in claim 1 wherein the units of the formulae (I) and (III) are in the form of pharmaceutically acceptable salts according respectively to the units of the formulae (V) and (IV).

5. The copolymer defined in claim 3 wherein the units of the formulae (I) and (III) are in the form of pharmaceutically acceptable salts according respectively to the units of the formulae (V) and (IV).

* * * * *